United States Patent
Nikolski et al.

(10) Patent No.: US 9,814,887 B2
(45) Date of Patent: Nov. 14, 2017

(54) SELECTION OF OPTIMAL ACCELEROMETER SENSING AXIS FOR RATE RESPONSE IN LEADLESS PACEMAKER

(71) Applicant: Medtronic, Inc., Minneapolis, MN (US)

(72) Inventors: Vladimir P Nikolski, Blaine, MN (US); Todd J Sheldon, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 127 days.

(21) Appl. No.: 14/174,514

(22) Filed: Feb. 6, 2014

(65) Prior Publication Data
US 2015/0217119 A1    Aug. 6, 2015

(51) Int. Cl.
| A61B 5/0402 | (2006.01) |
| A61B 5/00 | (2006.01) |
| A61B 5/11 | (2006.01) |
| A61N 1/365 | (2006.01) |
| A61N 1/375 | (2006.01) |

(52) U.S. Cl.
CPC ........ *A61N 1/36542* (2013.01); *A61B 5/0402* (2013.01); *A61B 5/1116* (2013.01); *A61B 5/1121* (2013.01); *A61B 5/4836* (2013.01); *A61N 1/36535* (2013.01); *A61N 1/3756* (2013.01)

(58) Field of Classification Search
CPC .. A61N 1/36542; A61B 5/1116; A61B 5/4836
USPC ....................................................... 600/595
See application file for complete search history.

(56) References Cited

U.S. PATENT DOCUMENTS

| 761,162 A | 5/1904 | Gold |
| 4,374,382 A | 2/1983 | Markowitz |
| 4,476,868 A | 10/1984 | Thompson |
| 4,485,813 A | 12/1984 | Anderson et al. |
| 5,052,388 A | 10/1991 | Sivula et al. |
| 5,074,302 A | 12/1991 | Poore et al. |
| 5,117,824 A | 6/1992 | Keimel et al. |
| 5,154,170 A | 10/1992 | Bennett et al. |
| 5,165,404 A | 11/1992 | Andersson et al. |
| 5,165,405 A | 11/1992 | Elkwall |

(Continued)

FOREIGN PATENT DOCUMENTS

| CN | 1838076 A | 9/2006 |
| CN | 1838076 A | 9/2006 |

(Continued)

OTHER PUBLICATIONS

C00006177.USU1, U.S. Appl. No. 14/552,758, filed Nov. 25, 2014.

(Continued)

*Primary Examiner* — Michael C Stout
*Assistant Examiner* — Nicholas E Kolderman

(57) ABSTRACT

A medical device and associated method record signals from each real axis of a multi-axis sensor. An optimal axis for monitoring a physiological signal of the patient is identified from the real axes of the multi-axis sensor and multiple virtual axes. Coordinates defining the optimal axis are stored as respective weighting factors of the signals from each real axis of the multi-axis sensor. A metric of the physiological signal is determined using the multi-axis sensor signals and the weighting factors.

21 Claims, 6 Drawing Sheets

(56) References Cited

U.S. PATENT DOCUMENTS

| | | | |
|---|---|---|---|
| 5,172,690 A | 12/1992 | Nappholz et al. | |
| 5,190,034 A | 3/1993 | Sholder | |
| 5,222,493 A | 6/1993 | Sholder | |
| 5,226,413 A | 7/1993 | Bennett et al. | |
| 5,231,986 A | 8/1993 | Bennett | |
| 5,285,780 A | 2/1994 | Tsuji et al. | |
| 5,304,208 A | 4/1994 | Inguaggiato et al. | |
| 5,312,454 A | 5/1994 | Roline et al. | |
| 5,320,643 A | 6/1994 | Roline et al. | |
| 5,324,310 A | 6/1994 | Greeninger et al. | |
| 5,345,362 A | 9/1994 | Winkler | |
| 5,354,317 A | 10/1994 | Alt | |
| 5,423,867 A | 6/1995 | Poore et al. | |
| 5,447,525 A | 9/1995 | Powell et al. | |
| 5,496,351 A | 3/1996 | Plicchi et al. | |
| 5,507,782 A | 4/1996 | Kieval et al. | |
| 5,507,785 A | 4/1996 | Deno | |
| 5,562,711 A | 10/1996 | Yerich et al. | |
| 5,593,431 A | 1/1997 | Sheldon | |
| 5,601,615 A | 2/1997 | Markowitz et al. | |
| 5,609,612 A | 3/1997 | Plicchi et al. | |
| 5,628,777 A | 5/1997 | Moberg et al. | |
| 5,683,432 A | 11/1997 | Goedeke et al. | |
| 5,693,075 A | 12/1997 | Plicchi et al. | |
| 5,720,769 A | 2/1998 | van Oort et al. | |
| 5,755,740 A | 5/1998 | Nappholz | |
| 5,766,230 A | 6/1998 | Routh et al. | |
| 5,782,889 A | 7/1998 | Hognelid et al. | |
| 5,944,745 A | 8/1999 | Rueter | |
| 5,954,755 A | 9/1999 | Casavant | |
| 6,044,297 A | 3/2000 | Sheldon et al. | |
| 6,389,316 B1 | 5/2002 | Bornzin et al. | |
| 6,449,508 B1 | 9/2002 | Sheldon et al. | |
| 6,553,259 B2 | 4/2003 | Mouchawar et al. | |
| 6,772,005 B2 | 8/2004 | Casavant et al. | |
| 6,819,955 B2 | 11/2004 | Levine | |
| 6,950,704 B1 | 9/2005 | Bradley | |
| 7,031,772 B2 | 4/2006 | Condie et al. | |
| 7,076,283 B2 | 7/2006 | Cho et al. | |
| 7,130,690 B2 | 10/2006 | Rueter et al. | |
| 7,280,868 B2 | 10/2007 | Rueter et al. | |
| 7,400,924 B2 | 7/2008 | Rueter | |
| 7,457,666 B2 | 11/2008 | Bohn et al. | |
| 7,532,930 B2 | 5/2009 | Schermeier et al. | |
| 7,761,162 B2 | 7/2010 | Dong et al. | |
| 7,778,696 B2 | 8/2010 | Sathaye | |
| 7,783,355 B2 | 8/2010 | Rueter | |
| 7,818,059 B2 | 10/2010 | Rueter et al. | |
| 7,831,303 B2 | 11/2010 | Rueter et al. | |
| 8,280,509 B2 | 10/2012 | Sathaye | |
| 8,433,409 B2 | 4/2013 | Johnson et al. | |
| 8,532,785 B1 | 9/2013 | Crutchfield et al. | |
| 8,541,131 B2 | 9/2013 | Lund et al. | |
| 8,956,295 B2 | 2/2015 | Ni et al. | |
| 9,452,292 B2 | 9/2016 | Demmer et al. | |
| 2002/0183798 A1 | 12/2002 | Vonk | |
| 2003/0069611 A1 | 4/2003 | Levine | |
| 2003/0078624 A1 | 4/2003 | Carlson et al. | |
| 2003/0078627 A1 | 4/2003 | Casavant et al. | |
| 2003/0083700 A1 | 5/2003 | Hill | |
| 2003/0083712 A1 | 5/2003 | Rueter et al. | |
| 2003/0195579 A1 | 10/2003 | Bradley et al. | |
| 2003/0204214 A1 | 10/2003 | Ferek-Patric | |
| 2004/0030358 A1 | 2/2004 | Rueter et al. | |
| 2004/0088019 A1 | 5/2004 | Rueter et al. | |
| 2004/0260352 A1 | 12/2004 | Rueter et al. | |
| 2005/0015985 A1 | 1/2005 | Dvoskin | |
| 2005/0021095 A1 | 1/2005 | Rueter et al. | |
| 2005/0159785 A1 | 7/2005 | Rueter | |
| 2005/0222630 A1 | 10/2005 | Schermeier et al. | |
| 2006/0155338 A1 | 7/2006 | Mongeon et al. | |
| 2006/0241710 A1 | 10/2006 | Rueter | |
| 2006/0247705 A1 | 11/2006 | Rueter et al. | |
| 2006/0253156 A1 | 11/2006 | Pastore et al. | |
| 2007/0115277 A1 | 5/2007 | Wang et al. | |
| 2008/0195165 A1 | 8/2008 | Stahmann et al. | |
| 2010/0010380 A1 | 1/2010 | Panken et al. | |
| 2010/0010583 A1* | 1/2010 | Panken | A61B 5/1116 607/62 |
| 2011/0012759 A1 | 1/2011 | Yin | |
| 2011/0029034 A1 | 2/2011 | Fischer et al. | |
| 2011/0152963 A1 | 6/2011 | Stahmann et al. | |
| 2012/0065524 A1* | 3/2012 | Morren | A61B 5/1102 600/484 |
| 2012/0109259 A1 | 5/2012 | Bond et al. | |
| 2012/0172892 A1 | 7/2012 | Grubac et al. | |
| 2012/0245476 A1 | 9/2012 | Skerl et al. | |
| 2013/0035748 A1 | 2/2013 | Bonner et al. | |
| 2013/0079861 A1 | 3/2013 | Reinert et al. | |
| 2013/0090702 A1 | 4/2013 | Mongeon et al. | |
| 2013/0116602 A1 | 5/2013 | Van Den Heuvel et al. | |
| 2013/0150911 A1 | 6/2013 | Perschbacher et al. | |
| 2013/0211205 A1 | 8/2013 | Havel et al. | |
| 2013/0289652 A1 | 10/2013 | Skelton et al. | |
| 2015/0173655 A1 | 6/2015 | Demmer et al. | |
| 2015/0217119 A1 | 8/2015 | Nikolski et al. | |
| 2015/0238769 A1 | 8/2015 | Demmer et al. | |
| 2016/0144191 A1 | 5/2016 | Sheldon et al. | |

FOREIGN PATENT DOCUMENTS

| | | | |
|---|---|---|---|
| EP | 1116495 A2 | 7/2001 | |
| EP | 2239007 A1 | 10/2010 | |
| WO | WO 2004041086 A1 * | 5/2004 | A61B 5/1118 |

OTHER PUBLICATIONS (PCT/US2015/062137) Invitation to Pay Additional Fees and, where applicable, protest fee.
U.S. Appl. No. 14/174,514, filed Feb. 6, 2014.
(PCT/US2015/013729) PCT Notification of Transmittal of the International Search Report and the Written Opinion of the International Searching Authority.
(PCT/US2014/070598) PCT Notification of Transmittal of the International Search Report and the Written Opinion of the International Searching Authority.
Demmer, et al., "Method and Apparatus for Detecting Loss of Capture", U.S. Appl. No. 14/261,776, filed Apr. 25, 2014, 44 pages.
(PCT/US2014/067337) PCT Notification of Transmittal of the International Search Report and the Written Opinion of the International Searching Authority.
U.S. Appl. No. 14/552,758, filed Nov. 25, 2014.
(PCT/US2015/027055) PCT Notification of Transmittal of the International Search Report and the Written Opinion of the International Searching Authority, mailed Sep. 30, 2015, 9 pages.
Telectronics Meta 1254 DDDr Physician Manual, Chapter 8 (46 pages).
Telectronics Meta 1254 DDDr Physician Manual (55 pages).
(PCT/US2015/062137) Invitation to Pay Additional fees and, where applicable, protest fee, mailed Mar. 1, 2016, 8 pages.
(PCT/US2016/049573) PCT Notification of Transmittal of the International Search Report and the Written Opinion of the International Searching Authority, dated Nov. 28, 2016, 10 pages.
U.S. Appl. No. 14/920,228, filed Oct. 22, 2015, 54 pages.

* cited by examiner

SELECTION OF OPTIMAL ACCELEROMETER SENSING AXIS FOR RATE RESPONSE IN LEADLESS PACEMAKER

TECHNICAL FIELD

The disclosure relates to implantable medical devices having multi-axis sensors and an associated method for determining an optimal signal derived from the multi-axis signals for monitoring a patient condition.

BACKGROUND

Numerous implantable medical devices (IMDs) are available for acute or chronic implantation within patients. Some implantable medical devices may be used to monitor physiological signals of the patient, such as cardiac pacemakers, implantable hemodynamic monitors, implantable cardiac monitors (sometimes referred to as implantable loop recorders or ECG monitors), implantable blood chemistry monitors, implantable pressure monitors, etc. Among the various types of physiological sensors utilized by medical devices for monitoring patients are electrodes for measuring electrical signals and/or impedances, piezoelectric crystals, accelerometers, pressure sensors, pH sensors, acoustical sensors, temperature sensors, oxygen sensors and more.

The physiological signals may be stored, processed and analyzed by the medical device to generate physiological data about a patient useful to a clinician in diagnosing a condition or planning medical treatment. Some implantable devices may be configured to deliver a therapy in conjunction with monitoring of physiological signals. Physiological signals may be processed and analyzed to determine when a therapy is needed or how a therapy needs to be adjusted to benefit the patient.

Therapies delivered by an implantable medical device can include electrical stimulation therapies, e.g., cardiac pacing, cardioversion/defibrillation shock pulses, or neurostimulation, and pharmacological or biological fluid delivery therapies.

In order to provide reliable physiological data needed for determining a medical risk, detecting pathological conditions, controlling automatic therapy delivery or generally producing data in a form useful to a clinician for diagnosis and prognosis, reliable sensor signals are required. For example, patient activity level may be determined from an accelerometer in order provide rate responsive pacing at a heart rate that meets the metabolic demand of the patient. An accelerometer signal may be subject to noise or motion not directly associated with the motion of patient activity or exercise, such as cardiac motion or respiratory motion. Methods are needed for identifying a sensor signal that provides acceptable signal to noise ratio for reliable signal processing.

DETAILED DESCRIPTION

Techniques are disclosed herein for selecting an optimal axis from a multi-axis sensor in an implantable or wearable medical device for monitoring a physiological signal. The optimal axis may be a real, physical axis of the sensor or a virtual axis of the sensor determined as a combination of two or more of the real axis signals. To illustrate the disclosed techniques, an IMD including a multi-axis accelerometer for monitoring patient activity is described herein with the accompanying drawings. In this example, the IMD processor is enabled to select an optimal axis from the real axis signals and virtual axis signals generated from the real axis signals for monitoring patient body motion indicative of patient activity. These and other aspects of the disclosed techniques are described herein. Examples of other types of devices and sensors are listed, however, without limitation, which may implement the disclosed techniques for selecting an optimal signal axis from among real and virtual axes for monitoring a physiological signal.

A change in the accelerometer orientation in devices having only a single-axis accelerometer may result in a low signal-to-noise ratio and poor discrimination between rest and activity and/or between different levels of activity. By providing a multi-axis accelerometer, the real physical or virtual axis being used to derive a patient activity metric from the accelerometer can be adjusted over time as needed. For example, if the orientation or position of the accelerometer changes over time, an initially-selected sensor axis may produce a signal having a reduced signal-to-noise ratio. Evaluation of multiple real and virtual axis signals enables a different axis signal to be selected with an improved signal-to-noise ratio.

Figure 1:
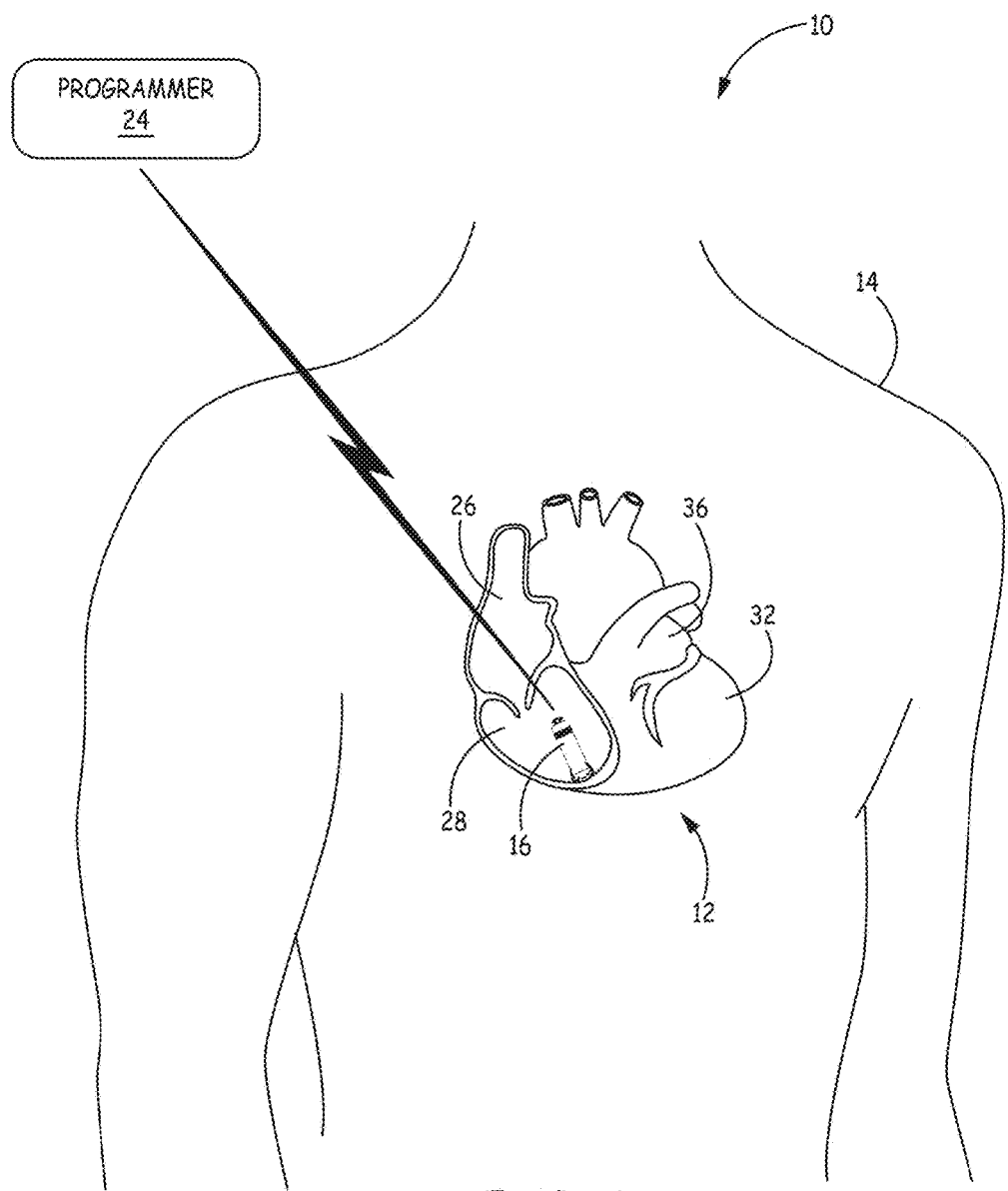
FIG. 1 is a conceptual diagram illustrating one therapy system that may be used to monitor one or more physiological parameters of a patient and provide therapy.

FIG. 1 is a conceptual diagram illustrating a medical monitoring and therapy delivery system 10 that may be used to monitor one or more physiological parameters of patient 14 and/or to provide therapy to heart 12 of patient 14. Therapy system 10 includes IMD 16, configured to communicate wirelessly with programmer 24. IMD 16 is an implantable leadless pacemaker that is capable of providing electrical signals to heart 12 via one or more electrodes (not shown in FIG. 1) on its outer housing. Additionally, IMD 16 may sense cardiac electrical signals attendant to the depolarization and repolarization of heart 12 via electrodes on its outer housing. In some examples, IMD 16 provides pacing pulses to heart 12 based on the cardiac electrical signals sensed within heart 12.

IMD 16 includes a set of active fixation tines to secure IMD 16 to a patient tissue. IMD 16 may include a set of active fixation tines as disclosed in commonly-assigned, pre-grant publication U.S. 2012/0172892 (Grubac, et al.), hereby incorporated herein by reference in its entirety. In the example of FIG. 1, IMD 16 is positioned wholly within heart 12 proximate to an inner wall of right ventricle 28 to provide right ventricular (RV) pacing. Although IMD 16 is shown within heart 12 and proximate to an inner wall of right ventricle 28 in the example of FIG. 1, IMD 16 may be positioned at any other location outside or within heart 12. For example, IMD 16 may be positioned outside or within right atrium 26, left atrium 36, and/or left ventricle 32, e.g., to provide respective right atrial, left atrial, and left ventricular sensing and pacing.

Depending on the location of implant, IMD 16 may include other stimulation functionalities. For example, IMD 16 may provide atrioventricular nodal stimulation, fat pad stimulation, vagal stimulation, or other types of neurostimulation. In other examples, IMD 16 may be a monitor that senses one or more parameters of heart 12 for patient monitoring purposes and may not provide any stimulation or therapy delivery functionality. In some examples, system 10 may include a plurality of leadless IMDs 16, e.g., to provide stimulation and/or sensing at a variety of locations.

FIG. 1 further depicts programmer 24 in wireless communication with IMD 16. In some examples, programmer 24 comprises a handheld computing device, computer workstation, or networked computing device. Programmer 24 includes a user interface that presents information to and receives input from a user. It should be noted that the user may also interact with programmer 24 remotely via a networked computing device.

A user, such as a physician, technician, surgeon, electrophysiologist, other clinician, or patient, interacts with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD 16. A user may use programmer 24 to retrieve information from IMD 16 regarding the rhythm of heart 12, trends therein over time, or arrhythmic episodes.

The user may use programmer 24 to retrieve information from IMD 16 regarding other sensed physiological parameters of patient 14 or information derived from sensed physiological signals, such as intracardiac or intravascular pressure, activity, posture, tissue oxygen levels, blood oxygen levels, respiration, tissue perfusion, heart sounds, cardiac electrogram (EGM), intracardiac impedance, or thoracic impedance. In some examples, the user may use programmer 24 to retrieve information from IMD 16 regarding the performance of IMD 16 or other components of system 10, such as the power source of IMD 16. As another example, the user may interact with programmer 24 to program IMD 16 including selecting control parameter values for patient monitoring and therapy delivery provided by IMD 16, such as pacing or neurostimulation.

IMD 16 and programmer 24 may communicate via wireless communication. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

In some examples, IMD 16 includes a three-dimensional accelerometer (not shown in FIG. 1) capable of producing motion signals in three different dimensions. For example, the accelerometer may produce signals corresponding to motion in three orthogonal axes, x, y and z. Upon implantation of IMD 16, the orientation of the three orthogonal axes relative to the patient's anatomy will be uncertain since rotation of the IMD 16 can occur during an implant procedure. Furthermore, the IMD 16 orientation relative to the patient's anatomy may change over time as the IMD 16 is subjected to cardiac motion, postural changes or other body movement. As such, an accelerometer axis providing the optimal signal-to-noise ratio for monitoring patient motion of interest may be unknown. An optimal axis will vary between patients and may vary within a given patient over time due to changes in position of IMD 16 relative to the patient's anatomy and/or changes in patient posture or other factors.

While a single-chamber leadless device is shown in FIG. 1, it is recognized that techniques disclosed herein may be implemented in numerous types of implantable medical devices or combinations of implantable medical devices configured for monitoring a patient and/or delivering a therapy. Techniques disclosed herein may be applied to any medical sensor or combination of sensors having multiple axes for sensing a signal used to monitor a patient. Such sensors may be included in cardiac monitors, hemodynamic monitors, pacemakers, implantable cardioverter defibrillators, neurostimulators, drug delivery pumps, or other medical devices that are implantable or worn by a patient. Examples of other physiological sensors that may be configured to sense a signal along two or more sensing axes include optical sensors, electrodes for sensing physiological electrical signals generated by the patient's body or for sensing bioimpedance, microphones or other acoustical sensors, micro electromechanical system (MEMS) sensors, pressure sensors, and sensors configured for producing signals correlated to blood flow or volume.

Figure 2:
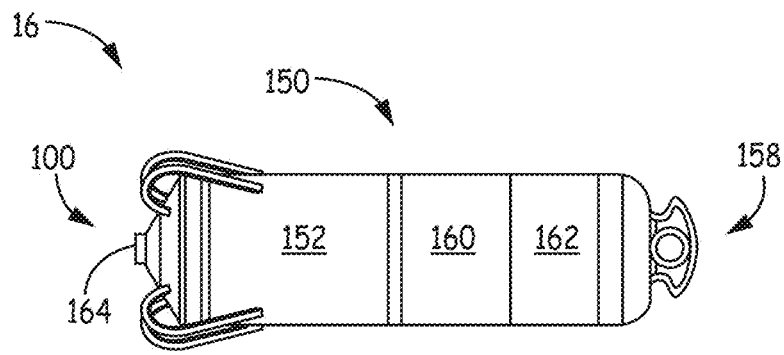
FIG. 2 is one example of an IMD in which techniques disclosed herein may be implemented.

FIG. 2 is a conceptual drawing of leadless IMD 16 including tine fixation and electrode subassembly 100, electronic subassembly 150 and delivery tool interface 158. Delivery tool interface 158 is located at the proximal end of electronic subassembly 150. Delivery tool interface 158 is configured to connect to a delivery device, such as a catheter, used to position IMD 16 during an implantation procedure, for example within a heart chamber.

Electronic subassembly 150 includes control electronics 152, which controls the sensing and therapy delivery functions (if available) of IMD 16, and battery 160, which powers control electronics 152. Battery 160 may include features of the batteries disclosed in commonly-assigned U.S. Pat. No. 8,433,409 (Johnson, et al.), the entire contents of which are incorporated by reference herein. As one example, control electronics 152 may include sensing circuitry, a stimulation generator and a telemetry module. Control electronics 152 includes a three-dimensional accelerometer in one embodiment for monitoring patient activity for use in controlling rate-responsive pacing in patient 14.

Tine fixation subassembly 100 is configured to anchor leadless IMD 16 to a patient tissue, such as a wall of heart 12, to position electrode 164 in operative proximity to a targeted tissue for sensing cardiac electrical signals and/or delivering electrical stimulation pulses. Tine fixation subassembly 100 is one example of a fixation member that may be used to stabilize the implant position of IMD 16. Numerous types of active and/or passive fixation members may be employed for anchoring or stabilizing IMD 16 in an implant position. When IMD 16 is advanced transvenously into the right ventricle, as shown in FIG. 1 for example, the orientation of IMD 16 may vary and the final orientation of an accelerometer included in control electronics 152 relative to the patient's anatomy may be unknown and may fluctuate with body movement and cardiac movement as described above. When the accelerometer is being used to monitor patient body motion to detect changes in activity as an indication of changes in metabolic demand, significant artifact will be present in the accelerometer signal due to cardiac motion. The techniques disclosed herein may be used to select an accelerometer axis for monitoring patient body motion that has an acceptable signal to noise ratio for distinguishing between different levels of patient activity in the presence of cardiac or other motion artifact that may confound the motion signal of interest.

The housings of control electronics 152 and battery 160 are formed from a biocompatible material, such as a stainless steel or titanium alloy. In some examples, the housings of control electronics 152 and battery 160 may include an insulating coating. Examples of insulating coatings include parylene, urethane, PEEK, or polyimide among others. Electronic subassembly 150 further includes electrode 162, which may include a low polarizing coating, such as titanium nitride, iridium oxide, ruthenium oxide among others. The entirety of the housings of control electronics 152 and battery 160 are electrically connected to one another, but only electrode 162 is uninsulated. In other examples, the entirety of the housing of battery 160 or the entirety of the housing of electronic subassembly 150 may function as an electrode instead of providing a localized electrode such as electrode 162. Alternatively, electrode 162 may be electrically isolated from the other portions of the housings of control electronics 152 and battery 160. Electrodes 162 and 164 form an anode and cathode pair for bipolar cardiac sensing and pacing.

Figure 3:
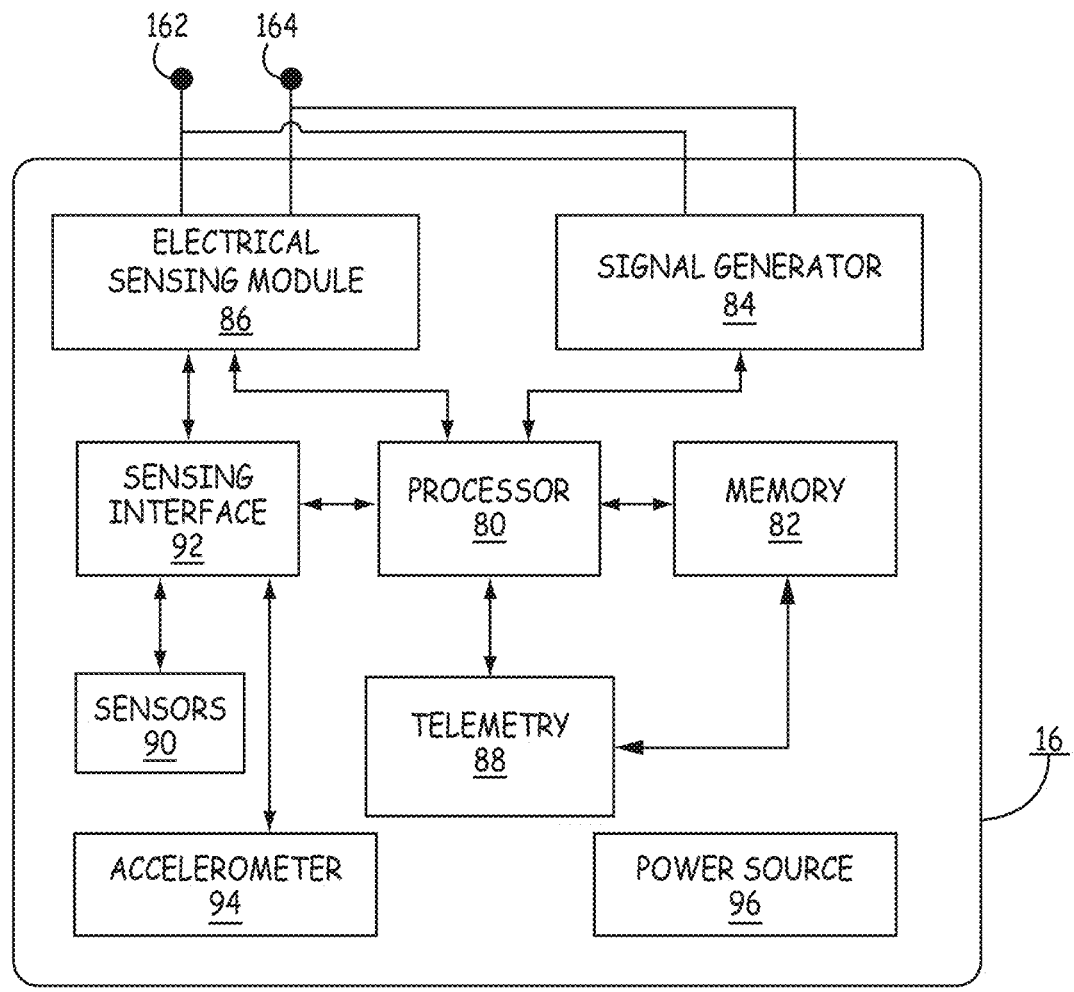
FIG. 3 is a functional block diagram of an example configuration of the IMD of FIG. 2.

FIG. 3 is a functional block diagram of an example configuration of IMD 16. IMD 16 includes a processor and control module 80, also referred to herein as "processor" 80 and associated memory 82, signal generator 84, electrical sensing module 86, and telemetry module 88. IMD 16 additionally includes a multi-dimensional accelerometer 94 for detecting patient body motion for monitoring patient activity. In various examples, accelerometer 94 may be implemented as a DC or AC accelerometer, a piezoelectric, piezoresistive or capacitive sensor or a micro electromechanical systems (MEMS) device.

IMD 16 optionally includes other physiological sensors 90, which may include pressure sensors, pH sensors, temperature sensors, acoustical sensors, flow sensors, oxygen sensors, or any other sensor used for producing a signal responsive to a time-varying physiological condition. Accelerometer 94 and sensors 90 are shown schematically within IMD 16, however it is recognized that accelerometer 94 and sensors 90 may alternatively be carried by a lead extending from IMD 16 or mounted along the exterior of the IMD electronic subassembly 152. Other sensors may include multiple sensing directions or axes for which the techniques disclosed herein may be adapted for determining an optimal axis.

A power source 96 provides power to each of the other modules and components of IMD 16 as required. Processor 80 may execute power control operations to control when various components or modules are powered to perform various IMD functions. Power source 96 may include one or more energy storage devices, such as one or more rechargeable or non-rechargeable batteries. Processor 80 may also be configured to perform diagnostic testing of IMD 16, which may include monitoring the remaining charge of power source 96 and providing a replacement or recharge indicator, for example. The connections between power source 96 and processor 80 and other IMD modules and components are not shown for the sake of clarity.

Modules 80, 84, 86, 88, 92, memory 82, sensors 90, and accelerometer 94 shown in FIG. 3 may include any discrete and/or integrated electronic circuit components that implement analog and/or digital circuits capable of producing the functions attributed to IMD 16 herein. For example, sensing module 86, sensing interface 92, and processor and control module 80 may include analog circuits, e.g., amplification circuits, filtering circuits, and/or other analog circuitry for receiving and processing signals from electrodes 162 and 164, sensors 90 and accelerometer 94. Electrical sensing module 86, sensing interface 92 and processing and control module 80 may also include digital circuits, e.g., combinational or sequential logic circuits, memory devices, A/D converters, etc. for processing received signals.

The functions attributed to IMD 16 herein may be embodied as one or more processors, hardware, firmware, software, or any combination thereof. Processor and control module 80 may include any one or more of a microprocessor, a controller, a digital signal processor (DSP), an application specific integrated circuit (ASIC), a field-programmable gate array (FPGA), or equivalent discrete or integrated logic circuitry. Depiction of different features of IMD 16 as discrete modules or components is intended to highlight different functional aspects and does not necessarily imply that such modules must be realized by separate hardware or software components. Rather, functionality associated with one or more modules may be performed by separate hardware or software components, or integrated within common or separate hardware or software components. For example, sensing interface 92 for receiving and converting analog electrical signals received from other IMD modules or sensors including accelerometer 94 may be implemented in hardware and software included in processor 80 and memory 82.

In some examples, sensing interface 92 is configured to receive one or more analog signals from electrical sensing module 86, sensors 90, and/or accelerometer 94. Sensing interface 92 includes an A/D converter for converting analog signals to digital signals. Processor 80 receives the converted digital signals and may analyze the digital signals for detecting a patient condition, controlling a therapy delivered by signal generator 84, and/or storing patient data in memory 82 for later transmission to programmer 24 via telemetry module 88.

Memory 82 may include computer-readable instructions that, when executed by processor 80, cause IMD 16 and processor 80 to perform various functions attributed throughout this disclosure to IMD 16, processor 80, and sensing interface 92. The computer-readable instructions may be encoded within memory 82. Memory 82 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal.

Electrical sensing module 86 receives cardiac electrical signals from electrodes 162 and 164 for sensing cardiac electrical events, e.g. P-waves and R-waves, in order to monitor electrical activity of heart 112. Sense event signals produced by sensing module 86 are used by processor 80 to determine a need for therapy delivery.

Processor and control module 80 includes a therapy control module that controls signal generator 84 to deliver electrical stimulation therapy, e.g., cardiac pacing, to heart 12 according to a selected one or more therapy programs, which may be stored in memory 82. Signal generator 84 is electrically coupled to electrodes 162 and 164, to deliver electrical stimulation therapy to heart 12. Signal generator 84 delivers cardiac pacing pulses according to therapy control parameters and responsive to signals sensed by electrical sensing module 86, sensors 90 (if present), and accelerometer 94. Memory 82 stores intervals, counters, or other data used by processor 80 to control the delivery of pacing pulses by signal generator 84. In one example, IMD 16 is a rate responsive pacemaker that utilizes a patient activity metric derived by processor 80 from a signal received from accelerometer 94 for controlling a rate of pacing therapy delivery by signal generator 84.

Accelerometer 94 may be bonded to an inner surface of the control electronics enclosure or incorporated on an internal substrate. A pacemaker arrangement including a piezoelectric accelerometer for detecting patient motion is disclosed, for example, in U.S. Pat. No. 4,485,813 (Anderson, et al.) and U.S. Pat. No. 5,052,388 (Sivula, et al.), both of which patents are hereby incorporated by reference herein in their entirety. Examples of three-dimensional accelerometers used for sensing patient activity and/or posture are generally described in U.S. Pat. No. 5,593,431 (Sheldon), and U.S. Pat. No. 6,044,297 (Sheldon), both of which are hereby incorporated herein by reference in their entirety. The disclosed techniques for selecting a sensor signal axis can be implemented in conjunction with a variety of three-dimensional accelerometers. Generally, three one-dimensional accelerometers are arranged to respond to acceleration in three different axes, typically but not necessarily orthogonal axes, in three dimensional space.

An accelerometer signal used for monitoring patient activity may be analyzed for providing a sensor-indicated pacing rate for controlling rate responsive cardiac pacing according to patient metabolic demand. An activity metric or index is derived from the accelerometer signal that is correlated to metabolic demand. Generally, the sensor-indicated pacing rate is computed from the activity metric within upper and lower pacing rate bounds to maintain a heart rate that meets the patient's metabolic need. Control of rate responsive pacing using an activity sensor is generally disclosed in commonly-assigned U.S. Pat. No. 7,031,772 (Condie, et al.), hereby incorporated herein by reference in its entirety.

An accelerometer signal may additionally or alternatively be used for monitoring patient activity for other patient monitoring, therapy control or diagnostic purposes. For example, it may be desirable to detect predetermined resting or active states of the patient to trigger monitoring of other physiological sensor signals, trigger therapies or adjustments to therapies, perform testing, etc. Accelerometer 94 may additionally or alternatively be used to determine patient posture, cardiac motion, respiratory motion or other physiological movement for use in monitoring the patient and/or controlling an IMD delivered therapy.

As described below, processor 80 may automatically adjust a therapy delivery rate and automatically adjust therapy control parameters based on patient activity monitoring performed using a selected accelerometer axis signal. The processor 80 is configured to evaluate a number of accelerometer axis signals, including virtual axes as described in detail below, and select an axis for monitoring patient activity. A patient activity metric is determined from the selected accelerometer axis signal at predetermined intervals of time. The therapy control module included in processor 80 adjusts a therapy control parameter in response to the metric.

In one embodiment, processor 80 generates a historical profile of the activity metric and automatically adjusts a control parameter used to set a target rate of therapy delivery in response to the historical profile. For example a historical level of the activity metric determined for non-strenuous activities of daily living may be used to set a target pacing rate for activities of daily living. In order to provide beneficial pacing rates, an accelerometer axis is selected to provide optimal discrimination between various activity levels including rest, activities of daily living, and more strenuous exercise or work.

Figure 4:
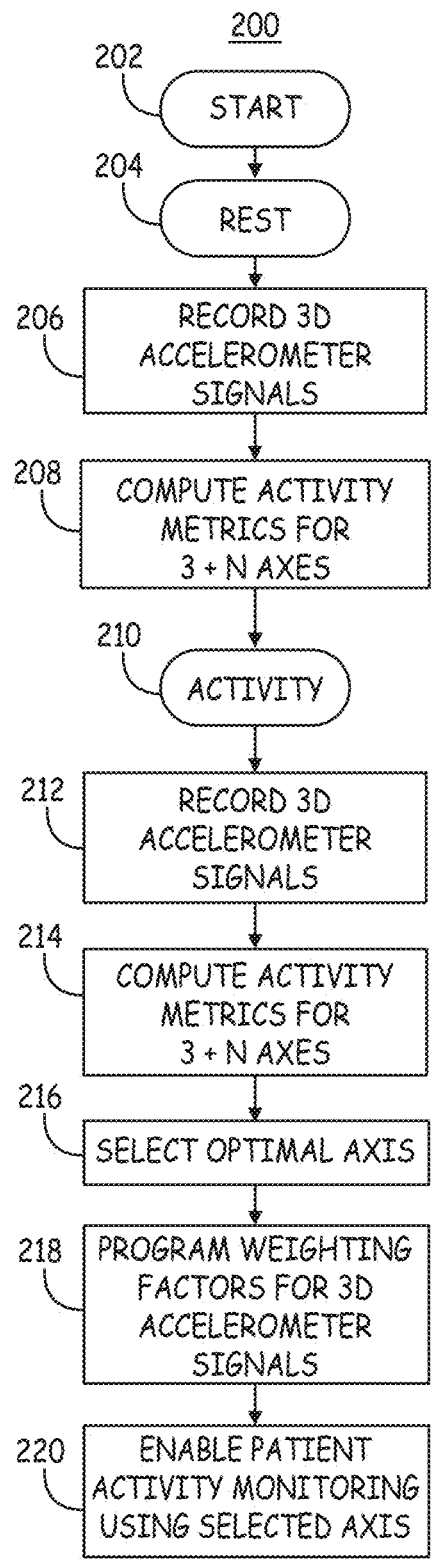
FIG. 4 is a flow chart of a method for selecting an accelerometer signal axis for monitoring a motion of a patient according to one embodiment.

FIG. 4 is a flow chart 200 of a method performed by processor and control 80 of IMD 16 for selecting an accelerometer signal axis according to one embodiment. The process is started at block 202, which may be manually initiated by a user or performed automatically, e.g., on a scheduled periodic basis.

The method described in conjunction with flow chart 200 and other flow charts presented herein relates primarily to a three-dimensional accelerometer used for monitoring patient activity. The three dimensions may be orthogonal axes corresponding to an x-axis, y-axis and a z-axis of the accelerometer where the orientation of these axes is unknown relative to a patient's anatomy or any other reference coordinate system. For the sake of convenience, the three axes of the accelerometer are referred to herein as the x-, y- and z-axes and are the "real" or "physical" axes of the accelerometer producing real axis signals. The three real axes, however, are not limited to being orthogonal axes. In various examples, a multi-axis accelerometer may be configured to sense motion along two or more orthogonal or non-orthogonal axes. While the illustrative examples presented herein relate to a three-dimensional accelerometer used for monitoring patient activity, it is contemplated that the techniques disclosed herein may be implemented in conjunction with multi-dimensional accelerometers used for monitoring other motion signals or with other types of multi-axis sensors used for monitoring other physiological signals of a patient.

At block 204, the IMD processor 80 determines if the patient is in a resting state. This determination may be made based on user input, time of day, or other physiological signals such as heart rate, respiration rate and/or posture. In one example a resting state is determined from an accelerometer axis signal. An accelerometer axis that is presently selected for monitoring patient activity or a predetermined nominal axis, which may be a physical x-, y- or z-axis or a combination of the available axis signals, may be used to detect rest. In one example, the first time the process of flow chart 200 is performed to select an axis for monitoring patient activity, a combination of the three orthogonal axes may be used to detect rest. In another example, the process shown is performed during an office visit under the care of a clinician, nurse or other caregiver. The patient may be instructed to rest in a laying or sitting position at block 204.

Upon establishing or detecting a resting state at block 204, the 3D accelerometer signals are received by the sensor interface 92 at block 206 and recorded for example by digitizing and storing the accelerometer signals in IMD memory 82. Recording of the 3D accelerometer signals may include transmission of the digital signals by telemetry module 88 to an external device, such as programmer 24, in real time or at a later time.

Figure 5A:
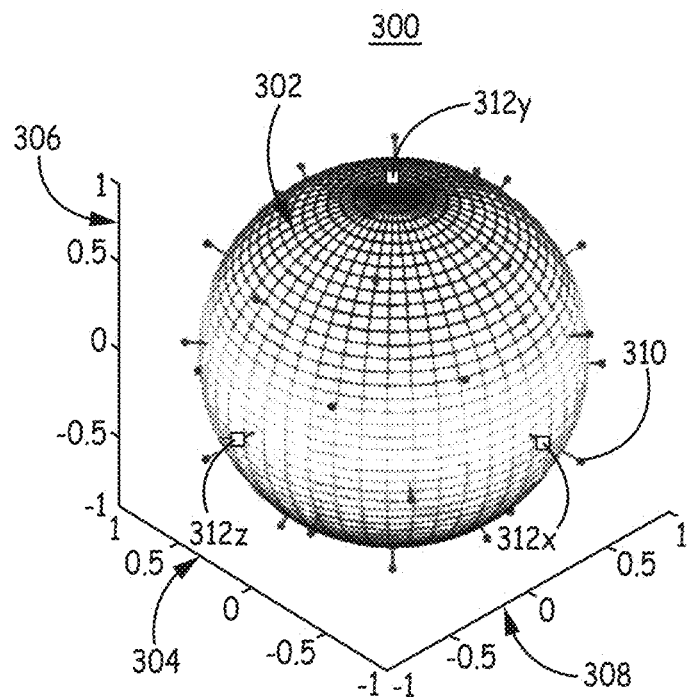
FIGS. 5A and 5B are example graphs illustrating virtual accelerometer axes uniformly distributed over the surface of a unit sphere.
Figure 5B:
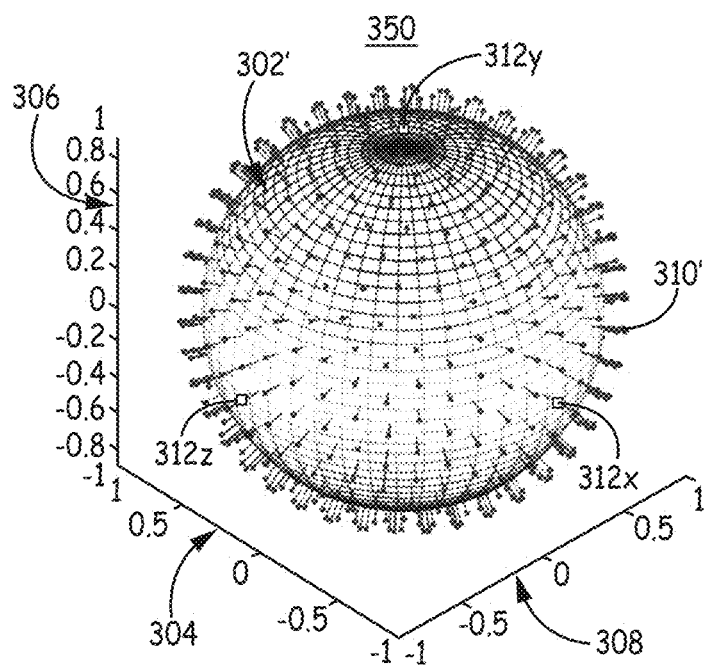

At block 208, activity metrics are computed for the patient's resting state for each of the three axes of the 3D accelerometer and for N virtual axes determined as weighted combinations of the three x-, y- and z-axis signals. The N virtual axes may be selected as uniformly distributed axes as described in conjunction with FIGS. 5A and 5B represented by weighted combinations of the three real accelerometer axis signals. Accordingly, a virtual axis signal may be computed as the sum of each of the real axis signals multiplied by respective weighting factors. An activity metric can then be computed from this virtual axis signal in the same manner as activity metrics are computed from the real x-, y- and z-axis signals.

Various activity metrics that are correlated to patient activity or metabolic demand may be derived from the accelerometer signals. In the illustrative embodiments described herein, the activity metric derived from an accelerometer signal is obtained by integrating the absolute value of a selected accelerometer axis signal over a predetermined time duration (such as 2 seconds). This metric is referred to herein as an "activity count" and is a representation of the amount of activity detected during the predetermined time interval. The 2-second (or other time interval) counts can be used directly to indicate patient activity in some embodiments or combined in further calculations to obtain other activity metrics. For example, the 2-second interval counts may be averaged or summed over multiple intervals to determine a patient activity level at a particular monitoring interval or for establishing an activity profile over a period of time.

One example of obtaining an activity count is disclosed in commonly-assigned U.S. Pat. No. 6,449,508 (Sheldon, et al.), incorporated herein by reference in its entirety. In another example, an activity count for use in rate responsive pacing is generally disclosed in U.S. Pat. No. 5,562,711 (Yerich, et al.), hereby incorporated herein by reference in its entirety. Briefly, an activity count is determined as a count of the number of times the accelerometer signal peak is greater than a predetermined threshold during a predetermined time interval. Other methods for using an accelerometer for monitoring patient activity for controlling pacing rate are generally disclosed in pre-grant U.S. Publication No. 2003/0078624 (Carlson, et al.).

After acquiring the resting accelerometer signals and determining rest metrics, the process advances to block 210 to wait for the patient's activity to change from the resting level to a non-resting or active level. The patient may be instructed by a caregiver to assume a prescribed level of activity, e.g. walking, jogging in place, controlled rate and incline on a treadmill, etc. A predetermined activity threshold may be defined which must be met in order to begin acquiring accelerometer signals at block 212. In one embodiment, the 3D accelerometer signals are recorded for one minute of rest at block 206 and one minute of walking at block 212. In other examples, the 3D accelerometer signals are recorded as the patient transitions from rest to activity, for example beginning from a resting state through a progressively increasing speed of treadmill walking up to a predefined maximum activity level (which may be sub-maximal exercise for the patient).

A non-resting activity metric is computed for each of the axes along the accelerometer x-, y- and z-axes and for the N virtual axes at block 214 for the non-resting state. The activity metrics may be computed by the IMD processor 80 in real time or offline after collecting accelerometer signal data for at least a resting state and one non-resting state. Alternatively, the activity metrics may be computed by a processor included in the external programmer 24 upon receiving the accelerometer signals from IMD 16. When a large number of virtual axes are being evaluated, the activity metrics may be computed by the external programmer 24 since it is likely to have significantly greater processing capacity than the IMD processor 80.

At block 216 an optimal activity monitoring axis is selected. In one example, selecting an optimal axis includes determining a ratio or difference between the resting metric and the non-resting metric for each of the 3+N axes. The axis having the greatest difference (or largest ratio) between the rest and non-rest metrics is selected for monitoring patient activity at block 216.

The axis having the greatest difference is expected to have the greatest signal-to-noise ratio and enable changes in activity to be reliably detected for use in controlling rate responsive pacing. Patient body motion indicative of activity is discernable from cardiac motion on the selected axis that has the greatest difference between a metric obtained at rest and one obtained during patient activity. A selected axis may also have the lowest metric at rest such that it has the lowest contribution of cardiac motion artifact to the signal.

In another example, selecting an optimal axis at block 216 may include identifying an axis signal having the least variation of all axis signals during a resting state. Numerous signal analysis techniques may be utilized to identify an axis having the least variation or an axis having a variation that is less than a specified threshold. Such techniques may include determining an activity count for each axis during a resting state and comparing the activity counts to identify a minimum value.

Principal Component Analysis (PCA) is another example of a technique that may be used to identify an axis having the least or minimal variation during rest. PCA performed on the 3D accelerometer signal may be performed on the raw axis signals without determining resting and non-resting activity level metrics at block 214 or on the activity counts determined over time from each axis signal. PCA may be performed to produce a selected axis that has minimal deviations during a cardiac cycle. For example, a third eigenvector determined during the resting state may be selected as an optimal axis since the third eigenvector will have the least variation during rest and therefore lowest contribution of the cardiac motion. An axis corresponding to the first eigenvector, i.e. the first principal component having the greatest variation at rest, will have the greatest contribution from cardiac motion and is avoided for monitoring patient activity.

In one example, singular value decomposition is applied to the mean-centered 3D accelerometer signal data acquired during rest. The first principal component represents the axis along which the greatest variation of the 3D signal occurs. During rest, this variation is primarily due to cardiac motion. The third principal component represents an axis along which the least variation occurs. This minimal variation along the third principal component is a strong indicator of the resting state of the patient with the confounding effect of cardiac motion minimized. During patient activity, increased variation along this third principal component is expected to be strongly correlated to the increased patient activity, enabling reliable detection and discrimination between patient activity states.

In other examples, other criteria may be applied to the resting and non-resting accelerometer signals and/or activity metrics under evaluation for selecting an optimal axis for patient monitoring. Other criteria may include comparisons between axes signals and/or comparisons to other sensor signals. In another example, selection of an optimal axis at block 216 may include determining the slope of the activity metrics derived from each axis as a patient transitions between a resting state and a predetermined maximum activity level. Controlled activity may be accomplished, for example, by instructing the patient to follow a specific treadmill exercise protocol. The activity metric slope may be determined for each of the 3+N axes. Axes having non-linear correlation with linear increase in treadmill workload may be rejected for use in monitoring patient activity. An axis producing a metric having a linear correlation with patient workload, a lowest metric value at rest, and greatest activity to rest ratio may be selected as the axis for monitoring patient activity at block 216.

At block 218, the coefficients of the x-, y- and z-axes that define the selected optimal axis are programmed in the IMD 16 for use as the weighting factors of the three accelerometer x-, y- and z-axis signals during patient activity monitoring. The optimal axis may be one of the accelerometer physical x-, y- or z-axes or any weighted combination of these axes. The IMD processor 80 includes hardware and/or software capable of processing the 3D accelerometer signal using the weighting factors for obtaining an activity signal from which a patient activity metric is derived. In the example of the intra-cardiac IMD 16, the optimal axis has the lowest cardiac motion artifact at rest and produces an activity metric having the greatest range between rest and the tested activity level. The processor 80 performs patient activity monitoring using the selected optimal axis signal at block 220 for controlling rate responsive therapy (and/or for other monitoring or therapy control applications).

FIG. 5A is an example graph 300 illustrating eighteen axes uniformly distributed over the surface of a sphere 302. A three dimensional coordinate system is defined by the x-axis 304, y-axis 306 and z-axis 308. The sphere 302 is centered on the origin of the coordinate system so that a virtual signal axis extending through the sphere origin and the surface of the sphere 302 is defined by a set of x-, y- and z-coordinates having values between −1 and +1. The three real accelerometer axes extend through real axis points 312x, 312y and 312z. Fifteen virtual axes extend through virtual axis points 310, not all of which points are visible in the view shown in FIG. 5A. The virtual axis points 310 shown in FIG. 5A include points on both ends of each virtual axis. The Cartesian coordinates defining a point 310 define the direction of a particular virtual axis and the weighing factors that are applied to the real x-, y- and z-axis signals of the accelerometer to derive a virtual axis signal.

The virtual axis signals are evaluated, along with the three physical axis signals as described in conjunction with FIG. 4, for selection of an optimal axis signal for patient activity monitoring. If a virtual axis signal is selected for patient monitoring, the x-, y- and z-coordinates defining the axis are stored in memory 82. Processor 80 uses the stored coordinates as the weighting factors applied to the physical x-, y- and z-signals to produce a virtual 3D accelerometer signal for deriving activity metrics from. The activity metrics may be used to compute a sensor indicated pacing rate for controlling rate-responsive pacing.

Numerous algorithms may be employed for generating a set of virtual axes. The algorithm used may be selected based on a desired spatial resolution of the virtual axes. The algorithm is generally selected to provide virtual axes that are distributed in all directions from an origin of a three-dimensional coordinate system with a desired spatial resolution. In some examples, the virtual axes are uniformly distributed and determined using repeatable, verifiable techniques. Since the IMD orientation may be arbitrary after implantation, the optimal axis may occur in any quadrant. In other examples, the virtual axes could be randomly determined and/or non-uniform.

In one example, the coordinate values of uniformly distributed points 310 defining virtual axes are generated through iterative computations with three real, physical axes fixed and all the remaining points 310 allowed to drift. An example list of x-, y- and z-coordinates computed to generate 15 uniformly distributed virtual axes, along with the three real, physical axes, is listed in TABLE I. The 15 virtual axes defined by the computed coordinates and the three real, physical axes of the accelerometer provide 18 axes along which a real or virtual accelerometer signal is produced.

TABLE I

Example three dimensional coordinates defining virtual accelerometer signal axes.

| X | Y | Z |
|---|---|---|
| 1 | 0 | 0 |
| 0 | 1 | 0 |
| 0 | 0 | 1 |
| 0.315 | 0.448 | −0.836 |
| −0.446 | −0.341 | −0.828 |
| −0.341 | −0.828 | −0.446 |
| 0.448 | −0.836 | −0.315 |
| 0.836 | 0.315 | −0.448 |
| 0.630 | 0.767 | −0.119 |
| −0.405 | 0.823 | −0.399 |
| −0.823 | 0.399 | 0.405 |
| −0.828 | −0.446 | −0.341 |
| −0.194 | −0.820 | 0.538 |
| 0.820 | −0.538 | 0.194 |
| 0.767 | −0.119 | 0.630 |
| −0.119 | 0.630 | 0.767 |
| −0.538 | 0.194 | 0.820 |
| −0.399 | −0.405 | 0.823 |

The coordinates are listed with an accuracy of 3 decimal points in TABLE I, however, it is recognized that the coordinates stored in the IMD memory 82 may be stored to an accuracy that is within reasonable processing power and speed of processor 80 and still provides acceptable signal quality.

FIG. 5B is an example graph 350 illustrating 255 virtual signal axes and three physical signal axes uniformly distributed over a sphere 302'. The points 312x, 312y, and 312z represent the real accelerometer axes. The points 310' define the direction of respective virtual axes extending through an origin of sphere 302' as described above. The coordinates of points 310' define the weighing factors that would be applied to the physical x-, y- and z-axis signals of the accelerometer if a virtual axis is selected for patient monitoring. As described above, points 310' include opposing points on either side of the origin through which a virtual axis extends and not all points are visible in the view shown. The weighting factors defined by points 310' are applied to the accelerometer signals received from each real axis of the 3D accelerometer to compute 255 different virtual axis signals. As suggested by FIGS. 5A and 5B, different densities or resolutions of virtual axes can be used for identifying an optimal monitoring axis. The number of virtual axes evaluated and compared to each other and the real physical axes may vary depending on the medical application and particular requirements of the IMD system.

For each of the computed "raw" virtual axis signals and for the three real axis signals of the accelerometer, an activity metric is computed for at least a resting state in some embodiments. The activity metric may be computed for a resting state and one predetermined non-resting state or multiple metrics may be computed as the patient transitions from a resting state to a non-resting state. A comparative analysis performed for selecting an optimal axis for patient activity monitoring may include determining an axis signal that has minimal variation (in the raw signal or in an activity count) during rest, an axis signal that has a maximum difference in variation between the resting state and a non-resting state, and/or an axis producing a signal having a linear correlation with changes in patient workload.

Figure 6:
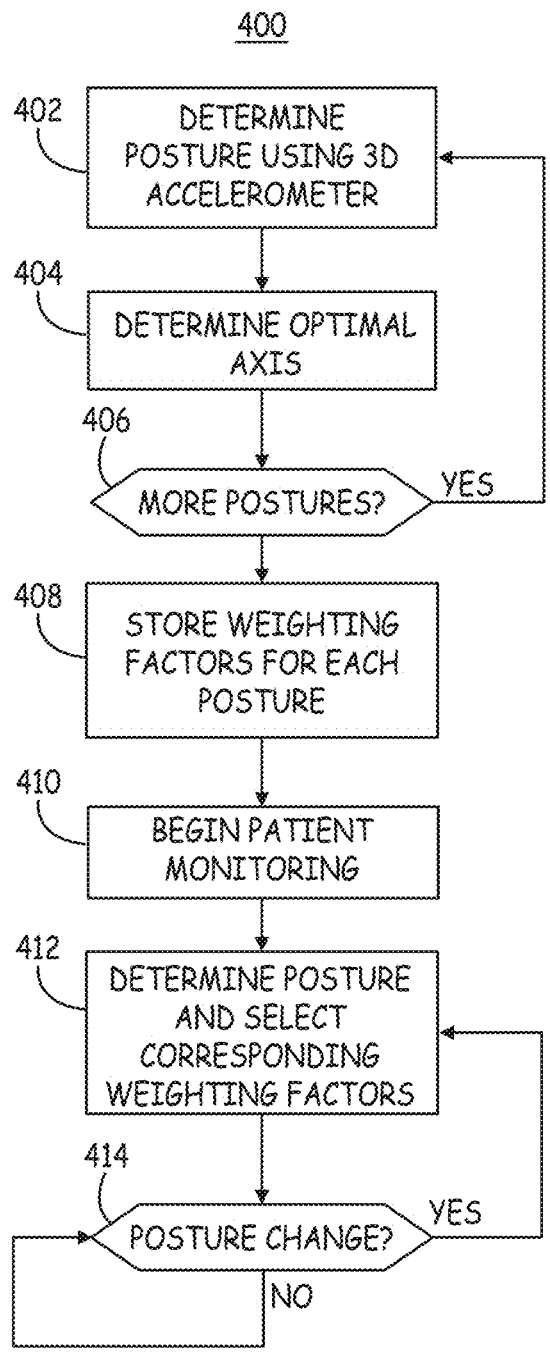
FIG. 6 is a flow chart of a method for selecting an accelerometer axis for monitoring patient activity according to another embodiment.

FIG. 6 is a flow chart 400 of a method for selecting an axis for monitoring patient activity according to another embodiment. The process is started at block 402 by determining the 3D accelerometer signal for a given patient posture. As patient posture changes, the optimal axis for sensing patient motion may change. The contribution of cardiac motion may change as posture changes and/or the contribution of patient body motion to the signal may change as posture changes leading to different signal-to-noise ratios on a given axis (virtual or real) for different postures. As such, an optimal axis may be selected for different patient postures.

The 3D accelerometer signal determined using equal weighting of the three real accelerometer x-, y- and z-axes may be used to represent a given posture. The actual posture need not be known by the IMD so a prescribed orientation of the accelerometer relative to the patient's anatomy is not required. Rather, for a given posture signal, determined from the equal weighting of the 3D axis, an optimal activity signal axis is identified so that each time a given posture signal is detected, the optimal activity signal axis can be selected for monitoring patient activity, e.g. as long as the posture signal remains within a predefined range.

The patient may be asked to assume a particular posture, e.g. a supine position, at block 402. The processor determines and stores the 3D accelerometer signal produced during the assumed posture. An optimal activity sensing axis is identified for the assumed posture at block 404 using the techniques described above in conjunction with FIG. 3. For example, in a supine position, resting level metrics may be determined for all real and virtual axes and an optimal axis may be selected based on the resting level metrics only. The patient may then be asked to assume another position at block 406 and the process is repeated (blocks 404 and 406) for storing a 3D accelerometer posture signal for each posture and identifying an optimal axis to be stored in conjunction with the respective posture signals.

This process may be repeated for as many postures as desired such as prone, sitting upright, sitting reclined, sitting forward (e.g. as on a bicycle), standing, etc. The optimal axis for some postures may be based only on a resting metric since some postures may only likely to be assumed during a resting state. In other examples, the patient may be asked to perform activity in each posture, such as leg lifts while laying down, cycling while sitting and leaning forward, etc., to obtain activity metrics during both rest and activity at block 402. An optimal axis is then selected based on a difference, ratio and/or slope between resting and non-resting activity metrics or other defined criteria for optimal axis selection.

Once an optimal axis has been identified for all test (or automatically identified) postures, the weighting factors defined by the coordinates of each optimal axis are stored in the IMD for each posture signal at block 408. Patient activity monitoring begins at block 410. The patient posture signal is detected based on the accelerometer signal. The corresponding optimal axis weighting factors for the posture signal are selected at block 412. For example, the accelerometer signal that was stored for each posture at block 402 that most closely matches the present 3D accelerometer signal is used to identify the optimal axis to be used for activity monitoring. The weighting factors for the optimal axis are applied to the 3D accelerometer signal for computing a desired activity axis signal and deriving an activity metric.

The posture signal may be monitored periodically at block 414 and if a change is detected, the weighting factors for the optimal activity axis for the stored posture signal that best matches the current posture signal are selected for computing the activity metric. In this way, the weighting factors used for computing an activity metric from a 3D accelerometer signal may be dynamic as patient posture changes are detected.

Figure 7:
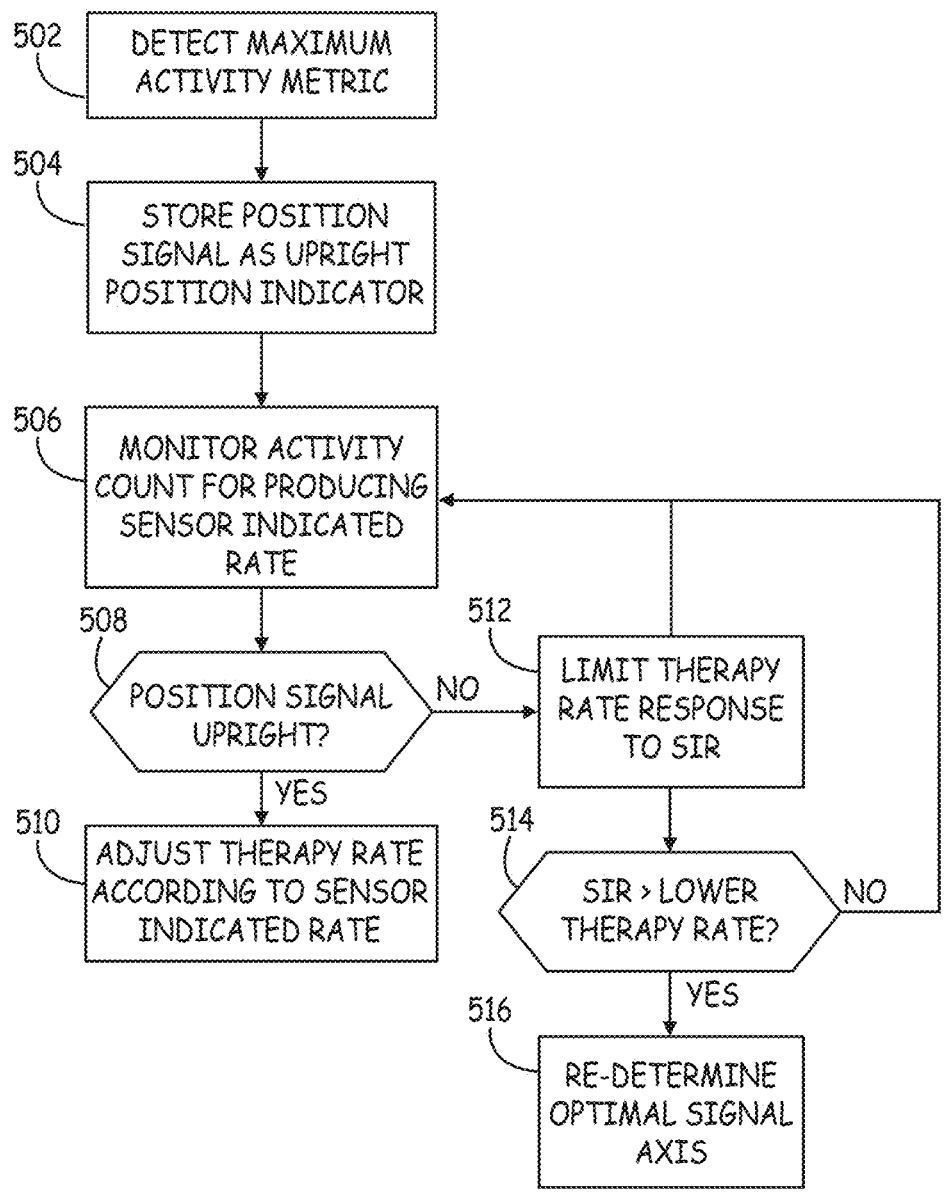
FIG. 7 is a flow chart of a method for controlling a therapy using a multi-axis sensor according to another example.

FIG. 7 is a flow chart 500 of a method for controlling a therapy using a multi-axis sensor according to another example. In some applications, it may be reasonable to assume that at times of highest activity counts, the patient is upright. When the activity count is relatively high, therefore, the patient posture is assumed to be upright, and the 3D accelerometer signal may be stored for this upright position as an "upright position signal."

In FIG. 7, if a maximum activity metric is detected at block 502, the 3D accelerometer signal is stored as an indication of an upright position at block 504. The "maximum" activity metric detected at block 502 may be a metric exceeding a predefined threshold or may be a maximum activity metric detected over a predetermined monitoring interval, e.g. over 24 or 48 hours or another time interval during which a high level of activity or exertion characteristic of the given patient is expected to be captured. This stored upright position signal may be the 3D signal from the accelerometer with equal weightings applied to each real axis signal.

Anytime the 3D accelerometer signal, used as a posture signal, deviates from the stored "upright" signal, the processor 80 detects a non-upright position of the patient. This discrimination between upright and non-upright positions without further specificity may be adequate in changing between an optimal axis for upright postures and an optimal axis for non-upright postures. During periods of time that an upright position signal is detected, an optimal signal axis for monitoring activity can be determined according to the methods described in conjunction with FIG. 4. Likewise, during period of time that the upright position signal is not detected, an optimal signal axis for monitoring activity during non-upright positions is determined.

Discrimination between upright and non-upright positions may also be used to control the rate response performance of the IMD in controlling a therapy rate based on a sensor indicated rate (SIR) produced from an activity count. Since rate responsive pacing is expected to be adequate at or near the lower pacing rate nearly all the time that the patient is not upright (i.e. in a resting position), discrimination between an upright position and a non-upright position, without further specificity of the positions, may be adequate for controlling therapy rate in combination with activity counts.

The activity count is monitored at block 506 using an optimal axis signal selected using the techniques disclosed above. The activity count is used to produce a sensor indicated therapy rate, e.g. a cardiac pacing rate used to control therapy delivery by the IMD 16. The position signal may be monitored continuously or periodically at block 508 to determine if the patient is in an upright or non-upright position based on a comparison of the current position signal (the 3D accelerometer signal) to the upright position signal stored in memory at block 504. If the position is determined to be upright, the therapy rate is adjusted by the processor 80 according to the sensor indicated rate at block 510 based on activity count monitoring.

If the position signal does not match the upright signal at decision block 508, however, the therapy rate may be limited at block 512. In rate responsive cardiac pacing, if the patient is not upright, a pacing rate at or near the lower rate is generally adequate. If the 3D accelerometer signal does not correspond to the upright position signal, the patient is determined to be in a non-upright position and is likely in a resting or non-active state. An activity count that results in a sensor indicated rate that is greater than a threshold level above the lower rate may be ignored when the patient is determined to be in a non-upright position. The patient is presumed to be resting or engaged in very low level activity not requiring an increase in pacing support. Accordingly, a therapy response to an activity metric may be limited based upon a determined patient position at block 512. For example, the pacing rate may be kept at the lower rate or within threshold level above the lower rate. In some patients, this feature could be disabled if the patient is known to perform inclined activity, such as swimming, on a regular basis.

If activity counts accumulated in a non-upright position produce a sensor indicated rate that is more than a threshold level above the lower pacing rate, as determined at block 514, a re-evaluation of accelerometer signal axes may be performed or a different axis signal may be selected for determining the activity metric as indicated at block 516.

It is recognized that the techniques disclosed in the flow charts presented herein may be combined in different combinations than shown and described here. For example, various combinations of data collection and various techniques for selecting an optimal axis may be used for evaluating and selecting an accelerometer axis for patient monitoring other than the specific examples described herein.

Thus, various embodiments of a medical device and method have been described for selecting an axis of a multi-dimensional sensor for monitoring a patient. However, one of ordinary skill in the art will appreciate that various modifications may be made to the described embodiments without departing from the scope of the following claims.

The invention claimed is:

1. A method for automatically monitoring a patient by an implantable medical device, comprising:
   receiving signals from each real axis of a multi-axis sensor by a processor of the implantable medical device;
   generating from the real axis signals a virtual signal for each of a plurality of virtual axes of the multi-axis sensor;
   determining a first value of an activity metric during a first activity state of the patient for each of the real axis signals and each of the virtual signals;
   determining a second value of the activity metric during a second activity state of the patient for each of the real axis signals and each of the virtual signals;
   identifying by the processor an optimal signal axis from the real axes and the plurality of virtual axes for monitoring a physiological signal of the patient by identifying one of the real axis signals and the virtual signals having at least one of a lowest variation of the first value of the activity metric during the first activity state and a greatest difference between the first value and the second value of the activity metric;
   storing a set of coordinates defining the optimal axis as respective weighting factors of the signals received from each real axis of the multi-axis sensor;
   monitoring the physiological signal of the patient by determining a third value of the activity metric using the multi-axis sensor signals and the stored weighting factors; and
   controlling a rate of delivering a therapy to the patient by a signal generator of the implantable medical device based on the third value of the activity metric.

2. The method of claim 1, wherein the multi-axis sensor is an accelerometer and further comprising:
   computing by the processor an activity metric for each real axis of the accelerometer and for the plurality of virtual axes of the accelerometer; and
   identifying the optimal axis by a comparative analysis of the activity metrics.

3. The method of claim 2, wherein the activity metrics are determined for each real axis and for each of the plurality of virtual axes during at least two different activity states of the patient comprising the first activity state and the second activity state, wherein the first activity state is a resting state.

4. The method of claim 3, wherein the comparative analysis comprises determining at least one of a difference, a ratio and a slope between the activity metrics for the at least two different activity states for each of the real axes and the plurality of virtual axes.

5. The method of claim 1, wherein the first activity state is a resting state and identifying the optimal axis comprises identifying an axis producing a lowest variation of the first value of the activity metric during the resting state of the patient.

6. The method of claim 1, further comprising:
   sensing a posture signal;
   identifying by the processor an optimal axis from the real axes and the plurality of virtual axes for monitoring the physiological condition of the patient during the sensed posture signal; and
   storing the posture signal and a set of coordinates defining the optimal axis as respective weighting factors to be applied to the signals received from each real axis of the multi-axis sensor when the posture signal is detected.

7. The method of claim 6, further comprising:
   monitoring a current posture signal;
   detecting a change from the current posture signal; and
   selecting different weighting factors to be applied to the signals received from each real axis of the multi-axis accelerometer in response to detecting the change.

8. The method of claim 1, wherein generating the virtual signal for each of a plurality of virtual axes of the multi-axis sensor comprises determining coordinates for the plurality of virtual axes that are uniformly distributed along a sphere.

9. The method of claim 1, wherein the implantable medical device is implantable within the patient's heart, the method further comprising controlling the rate of delivering the therapy to the patient in response to the metric by controlling a rate of cardiac pacing pulses delivered by the signal generator via a cathode electrode coupled to the housing of the implantable medical device.

10. The method of claim 1, further comprising:
    producing a first patient position signal from the real axis signals in response to the metric;
    detecting a change from the first patient position signal; and
    limiting an increase in the therapy rate caused by the metric in response to detecting the change from the first patient position signal.

11. An implantable medical device, comprising:
    a multi-axis sensor having at least two real axes;

a therapy delivery module comprising a signal generator; and a processor configured to:
receive signals from each real axis of the multi-axis sensor;
generate from the real axis signals a virtual signal for each of a plurality of virtual axes of the multi-axis sensor;
determine a first value of an activity metric during a first activity state of the patient for each of the real axis signals and each of the virtual signals;
determine a second value of the activity metric during a second activity state of the patient for each of the real axis signals and each of the virtual signals;
identify an optimal axis from the real axes and the plurality of virtual axes for monitoring a physiological signal of the patient by identifying one of the real axis signals and the virtual signals having at least one of a lowest variation of the first value of the activity metric during the first activity state and a greatest difference between the first value and the second value of the activity metric;
store coordinates defining the optimal axis as respective weighting factors of the signals from each axis of the multi-axis sensor;
determine a third value of the activity metric of the physiological signal of the patient using the multi-axis sensor signals and the weighting factors; and
control a rate of delivering a therapy to the patient by the signal generator based on the third value of the activity metric.

12. The device of claim 11, wherein the multi-axis sensor is a multi-axis accelerometer and the processor is further configured to:
compute an activity metric for each axis of the accelerometer and for the plurality of virtual axes of the accelerometer; and
identify the optimal axis by a comparative analysis of the activity metrics.

13. The device of claim 12, wherein the activity metrics are determined for each axis and for each virtual axis during at least two different activity states of the patient comprising the first activity state and the second activity state, wherein the first activity state is a resting state.

14. The device of claim 13, wherein the comparative analysis comprises determining at least one of a difference, a ratio and a slope between the activity metrics for the at least two different activity states for each of the accelerometer axes and the virtual axes.

15. The device of claim 11, wherein the first activity state is a resting state and wherein the processor is configured to identify the optimal axis by identifying an axis producing a lowest variation of the first value of the activity metric during the resting state of the patient.

16. The device of claim 11, wherein the processor is further configured to:
receive a posture signal;
identify by the processor an optimal axis from the real axes and the plurality of virtual axes for monitoring the physiological signal of the patient during the sensed posture signal; and
store the posture signal and a set of coordinates defining the optimal axis as respective weighting factors to be applied to the signals received from each real axis of the multi-axis sensor when the posture signal is detected.

17. The device of claim 16, wherein the processor is further configured to:
monitor a current posture signal;
detect a change from the current posture signal; and
select different weighting factors to be applied to the signals received from each real axis of the multi-axis accelerometer in response to detecting the change.

18. The device of claim 11, wherein generating the virtual signal for each of a plurality of virtual axes of the multi-axis sensor comprises determining coordinates for the plurality of virtual axes that are uniformly distributed along a sphere.

19. The device of claim 11, further comprising a housing and at least a cathode electrode carried by the housing and coupled to the signal generator;
the processor further configured to control the rate of delivering the therapy by controlling a rate of cardiac pacing pulses delivered by the signal generator via the cathode electrode.

20. The device of claim 11, wherein the processor is further configured to:
produce a first patient position signal from the real axis signals in response to the metric;
detect a change from the first patient position signal; and
limit an increase in the therapy rate caused by the metric in response to detecting the change from the first patient position signal.

21. A non-transitory computer readable storage medium storing a set of instructions that cause a processor of an implantable medical device comprising a multi-axis sensor to:
receive signals from each real axis of the multi-axis sensor;
generate from the real axis signals a virtual signal for each of a plurality of virtual axes of the multi-axis sensor;
determine a first value of an activity metric during a first activity state of the patient for each of the real axis signals and each of the virtual signals;
determine a second value of the activity metric during a second activity state of the patient for each of the real axis signals and each of the virtual signals;
identify an optimal axis for monitoring a physiological signal of the patient from the real axes of the multi-axis sensor and the plurality of virtual axes by identifying one of the real axis signals and the virtual signals having at least one of a lowest variation of the first value of the activity metric during the first activity state and a greatest difference between the first value and the second value of the activity metric;
store coordinates defining the optimal axis as respective weighting factors of the signals from each real axis of the multi-axis sensor;
determine a third value of the activity metric of the physiological signal using the multi-axis sensor signals and the weighting factors; and
control a rate of delivering a therapy to the patient by a signal generator of the implantable medical device based on the third value of the activity metric.

* * * * *